US006281239B1

(12) United States Patent
Glassman

(10) Patent No.: US 6,281,239 B1
(45) Date of Patent: Aug. 28, 2001

(54) METHOD OF TREATING ONYCHOMYCOSIS

(75) Inventor: Daniel Glassman, New York, NY (US)

(73) Assignee: Bradley Pharmeaceuticals, Inc., Fairfield, NJ (US)

( * ) Notice: Subject to any disclaimer, the term of this patent is extended or adjusted under 35 U.S.C. 154(b) by 0 days.

(21) Appl. No.: 09/547,841

(22) Filed: Apr. 12, 2000

(51) Int. Cl.⁷ .............................................. A61K 31/4174
(52) U.S. Cl. ............................................................. 514/399
(58) Field of Search ..................... 514/482, 399

(56) References Cited

U.S. PATENT DOCUMENTS

| 4,295,567 | 10/1981 | Knudsen | 206/534 |
| 5,919,470 | 7/1999 | Valdez et al. | 424/401 |

FOREIGN PATENT DOCUMENTS

96/19186 * 6/1996 (WO) .

OTHER PUBLICATIONS

Friedman–Birnbaum et al., International Journal of Dermatology, 36(1), pp. 67–69 (abstract), 1997.*

* cited by examiner

*Primary Examiner*—Phyllis G. Spivack
(74) *Attorney, Agent, or Firm*—Merchant & Gould P.C.

(57) ABSTRACT

A method of treating onychomycosis is described which includes administration to an infected area around a nail of a patient a tissue softening composition containing urea and an antifungal composition in one or separate compositions, concurrently or non-concurrently. Also described is a kit which contains the unit dosage forms, a protective gel and appropriate dressings for ready application.

12 Claims, No Drawings

METHOD OF TREATING ONYCHOMYCOSIS

FIELD OF THE INVENTION

The present invention relates to the use of a combination of topical pharmaceutical compositions for treating onychomycosis. Onychomycosis refers to a fungal infection of the nail unit, defined as the nail matrix, bed or plate. These compositions include an antifungal agent and a potent tissue softening cream containing an effective amount of urea. These combinations may be topically applied concurrently or non-concurrently. The invention also relates to a kit for convenient use by a patient for treating onychomycosis. The kit includes a packet containing two dosage units of the above compositions, occlusive dressings and a protective gel.

BACKGROUND OF THE INVENTION

Urea has been long recognized as a cosmetic ingredient in formulations acting as a humectant and moisturizer. High concentrations of urea, such as 40%, are also known to have mild, antibacterial effect. At these strengths the antibacterial effects are said to be similar to those of antibiotics, with the further advantage that all the common organisms are susceptible and the possibility of resistant strains need not be seriously considered. There have been reports of keratolytic activity attributed to urea with the ability at high concentrations to solubilize and denature protein. Concentrated solutions of urea can change the conformation of protein molecules. A striking effect is upon the water-binding capacity of the horny layer of the skin: pieces of normal horny layer, or scales from ichthyotic or psoriatic skin that have been soaked in 30% urea solution take up much more water. This is important because in maintaining the flexibility of the horny layer and the softness of the skin, the water content of the horny layer matters much more than its oil content.

Fungal infections of the nail are notoriously difficult to treat. Traditional, topical therapies cannot penetrate the nail plate, and eradicate the infection in and under the nail bed; they are useful only in milder forms of the disease. Systemic antifungal drug therapy is associated with potentially harmful side effects. Since oral antifungals are distributed throughout the entire body, systemic side effects such as elevated liver enzymes, gastrointestinal disorders and skin rashes are not uncommon and may require expensive medical intervention and laboratory tests.

SUMMARY OF THE INVENTION

The present invention relates to methods for treating onychomycosis in humans. These methods include topically administrating to the nail area of a human in need of such treatment a safe and effective amount of an antifungal agent, and a safe and effective amount of a potent tissue softener. More particularly, the method involves concurrent or non-concurrent administration of an antifungal composition, and a potent tissue softening composition, optionally with an occlusive dressing and a protective gel.

Use of topical keratolytics, such as urea, improve drug penetration and effects a chemical debridement of the hypertrophic nail. The occlusive dressing enhances the drug penetration.

Accordingly, a first aspect of the present invention is a method for treating onychomycosis by administering either concurrently or non-concurrently to the nail area of a patient in need thereof: (a) a therapeutically effective amount of a tissue softening composition comprising an effective amount of urea and the balance being dermatologically acceptable excipients; and (b) an antifungal composition comprising a therapeutically effective amount of an antifungal agent and a pharmaceutically acceptable carrier.

The invention also relates to a convenience pack containing an antifungal cream and a cream containing an effective amount of urea for the treatment of onychomycosis.

Accordingly, a second aspect of the present invention is a kit to be used by a patient in need of treating onychomycosis, the kit including (a) a first unit dosage form of a tissue softening composition comprising an effective amount of urea and the balance being dermatologically acceptable excipients; (b) a second unit dosage form of an antifungal composition comprising an antifungal agent and a pharmaceutically acceptable carrier; (c) an occlusive dressing, such as an adhesive toe shield dressing, and (d) a protective gel, such as a petroleum jelly.

DETAILED DESCRIPTION OF THE INVENTION

The present invention is a method for treating or preventing onychomycosis. Such method includes administering to the nail area of a human in need of such treatment or prevention, a safe and effective amount of an antifungal composition and a safe and effective amount of a potent tissue softening composition containing an effective amount of urea, for example, from about 30 to 60 wt-%, preferably about 40–50 wt-%, and particularly about 40 wt-%.

The term "administering" as needed herein refers to any method which, in sound medical practice delivers the antifungal agent and the potent tissue softener, e.g., 40% urea, to be treated in such a manner so as to be effective in the treatment of onychomycosis. Preferably both these agents are administered topically in a single composition or in individual compositions.

The phrase "safe and effective amount", as used herein, means an amount of an antifungal agent, and a potent tissue softener, urea, used in combination with each other in the compositions and methods of the present invention, sufficient enough to significantly and positively modify the condition to be treated but low enough to avoid serious side effects, within the scope of sound medical advice. The safe and effective amount of the agents of the present invention will vary with the particular condition being treated, the severity of the condition, the duration of treatment, the nature of the concurrent or non-concurrent therapy, the specific agents employed, the particular pharmaceutically acceptable carriers utilized, and the like factors within the knowledge and expertise of the attending physician.

The method of the present invention typically involve administering the antifungal agent in an amount to cover the affected area. The specific preferred quantity of the antifungal agent depends upon the particular antifungal agent used and its pharmacology.

The method of the present invention typically involves administering the potent tissue softener, urea in an amount to cover the affected area The method of the present invention includes administering the antifungal agent and the potent tissue softening urea either concurrently or non-concurrently. The term "concurrently", as used herein means that the two agents are administered within twenty four hours or less of each other. The term "non-concurrently" as used herein, means that the two agents are administered more than twenty fours hours apart. The methods of the present invention in which the agents are administered concurrently comprise and dosing regimen in which part or all of the dosing agents are performed concurrently. Thus for example, concurrent dosing of the agents include:

1. Up to 360 days of administration of a pharmaceutical composition of the present invention.

2. Up to 360 days of a regimen wherein the potent tissue softening composition, 40% urea, is topically applied to the affected area, and covered with a non-occlusive bandage in the evening or morning and the antifungal composition is applied, vice versa, in the morning or evening.

3. Up to 360 days of administration wherein the potent tissue softening composition, 40% urea, and the antifungal composition are applied simultaneously under a non-occlusive bandage in the morning or evening.

4. Up to 120 days of administration wherein the potent tissue softening composition, 40% urea, and the antifungal composition are applied simultaneously under a non-occlusive bandage in the morning or evening followed by applying the two topical compositions, preferably creams, every other day for an additional 90 days.

The method of the present invention in which the agents are administered non-concurrently include, for example: 40 days of topically applying to the affected area the potent tissue softener, 40% urea, with an occlusive bandage followed by an additional 110 days of administration of an antifungal composition.

For the method of the present invention, the duration of administration of the agents during either concurrent or non-concurrent dosing will vary according to the specific extent of the onychomycosis being treated, but typically it is within the range of 90 to 210 days.

Topical Antifungal Agents

A pharmaceutical composition of the present invention includes topical antifungal agents. The term "topical antifungal agent" as used herein means any naturally-occurring, synthetic or semi-synthetic composition, or mixture thereof, which is safe for use in the methods of the present invention, and is effective in killing or substantially inhibiting the growth of fungi, including but not limited to dermatophytes or yeast, Epidermophyton, Microsporum, Trichophyton and *Candida albicans*, and others.

Antifungal agents useful herein include but are not limited to: topical creams, ointments, solutions, lacquers and gels containing as active agents, for example, amoroline, betadine, bifonazole, clotrimazole, econazole nitrate, isoconazole, ketoconazole, miconazole nitrate, naftifine hydrochloride, oxiconazole, sulfanazole, terbinafine, ticonazole, tolnaftate, and undecenoates. The above antifungal topical compositions are known to those skilled in the art. A preferred antifungal agent is miconazole nitrate.

In addition to the antifungal agent, a pharmaceutical composition of the present invention includes a tissue softening composition containing an effective amount of urea, which, in its most preferred aspect, is a 40% urea topical composition. The use of such high concentrations of urea combined with skin protectants of an oleaginous nature derived from petroleum and further combined with suitable emulsifiers and thickeners have been found to be effective for tissue softening, without the need of traditional preservatives.

The tissue softening composition used in the present invention is a semi-solid at room temperature but is easily absorbed into the stratum corneum. A preferred application of the formulation is a cream, which contains petroleum, based liquid and solid fractions as skin protectants. The 40% urea dermatological composition is described in U.S. Pat. No. 5,919,470, which patent is incorporated herein by reference.

In addition to containing about 40 wt-% of urea, the composition includes skin protectants which include a combination of semi-solid and liquid petroleum fractions. The semi-solid skin protectant is contained in about 5.5 to about 20 wt-% and includes petrolatum or a synthetic or semi-synthetic hydrocarbon of the same nature as petrolatum. Mixtures of such ingredients can also be used. The preferred semi-solid material is petrolatum, commercially available from a wide variety of sources.

The liquid portion skin protectant is a liquid petrolatum and contained in the composition in about 10 to about 20 wt-%. This material can include any synthetic or semi-synthetic oleaginous liquid fraction. A preferred embodiment is mineral oil, which is a liquid mixture of hydrocarbons obtained from petroleum.

Another preferred ingredient encompassed in the composition of the present invention is propylene glycol which may be contained up to about 5 wt-% in the composition, preferably in the range of from about 1 to about 5 wt-%.

Although not to be held by theory, it is believed that the mild antibacterial properties of the urea and propylene glycol allow the composition of the present invention to be free of conventional preservatives such as methyl paraben, propyl and butyl imidazolidinylurea, diazolidinylurea, methylchloroisothiazolinone and methylisothiazolinone.

Preferred tissue softening compositions employed in the present invention are for example:

| Ingredient | Approximate Wt - % |
|---|---|
| antifungal agent | 0–5 |
| urea | 40 |
| petrolatum or a synthetic or semi-synthetic hydrocarbon, or a semi-solid mixture thereof | 5.5–20 |
| liquid petrolatum or synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| water | balance |
| antifungal agent | 0–5 |
| urea | 40 |
| petrolatum or a synthetic or semi-synthetic hydrocarbon, or a semi-solid mixture thereof | 5.5–20 |
| liquid petrolatum or a synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| mixture of a carbomer and triethanolamine | 0.05–30 |
| water | balance |

If desired, the antifungal agent in an amount up to 5% as noted above may be incorporated in the above compositions to provide a single pharmaceutical composition of the present invention.

A typical formulation representing the particular and most preferred embodiment of the tissue softening composition is illustrated as follows:

| Ingredient | % W/W |
| --- | --- |
| Purified water | 36.149 |
| Urea USP | 40.000 |
| Carbopol 940 | 0.150 |
| Petrolatum | 5.940 |
| Mineral oil | 12.060 |
| Glyceryl stearate | 1.875 |
| Cetyl alcohol | 0.626 |
| Propylene glycol | 3.000 |
| Xanthan gum | 0.050 |
| Trolamine NF | 0.150 |
| TOTAL | 100.000 |

The present invention also includes a kit or dispenser container, e.g. a box or package, which includes the individual dosage regimens, a first unit dosage form of the 40% urea tissue softening composition and a second unit dosage form being the antifungal composition in individual containers. Both unit dosage forms are topically administered and are preferably creams.

The kit also includes an occlusive dressing, e.g. Bandages and may optionally include an applicator. A particular advantageous dressing is an adhesive toe shield dressing which is included in an individual container in the kit. The covering of the creams with the occlusive dressing helps the therapeutic agents penetrate the skin.

The kit further includes a protective gel in its own individual container. The protective gel is used to protect the healthy skin in contact with the damaged nail. The gel is preferably petroleum jelly, also known as white petroleum or white soft paraffin. Other similar occluding excipients may be used such as hydrophobic materials derived from natural or synthetic sources. Examples include lanolin, white ointment, petrolatum, and the like.

The kit also provides indicia for distinguishing between the first and second unit dosage forms. The indicia is a visible feature which makes each unit dosage form distinguishable.

The kit may include containers where the unit dosage forms are in the form of a tube. However, any conventional pharmaceutical container is suitable. Examples include bottles, jars, canisters and packets.

By way of example, a subject suffering from onychomycosis may use the kit or convenience pack as follows:

1. A.M. APPLICATION:
   A. Prior to application, carefully wash damaged toenail and surrounding skin; dry thoroughly.
   B. Apply a coating of the PROTECTIVE GEL on the skin surrounding the toenail plate, to protect the healthy skin in contact with the damaged nail.
   C. Use the enclosed applicator to apply a light coating of the tissue softening 40% urea composition over the entire damaged toenail, to soften nail tissue or, alternatively, to remove the nail, if desired.
   D. Apply a light coating of the ANTIFUNGAL cream over the entire damaged toenail or, alternatively, on the affected area (on top of the coating of the urea composition).
   E. Cover toenail with the TOE SHIELD dressing.
2. P.M. APPLICATION
   A. Pull back the top flap of the TOE SHIELD dressing.
   B. Use the enclosed applicator to apply a light coating of the urea composition over the entire damaged toenail, to soften nail tissue.
   C. Apply a light coating of the ANTIFUNGAL cream over the entire damaged toenail (on top of the coating of urea composition).
   D. Re-cover toenail with TOP SHIELD dressing.
3. MORNING OF NEXT DAY
   A. Discard used TOE SHIELD dressing.
   B. Repeat above steps, A through D, for A.M. APPLICATION.
   C. Cover toenail with a new TOP SHIELD dressing.

What is claimed is:

1. A topical antifungal composition for treating onychomycosis consisting essentially of up to 5 wt.% of an antifungal agent in admixture with a tissue softening composition, wherein the tissue softening composition comprises:
   (a) about 40 wt-% urea;
   (b) about 5.5 to about 20 wt-% petrolatum or a synthetic or semi-synthetic hydrocarbon, or a semi-solid mixture thereof;
   (c) about 10 to about 20 wt-% of a liquid petrolatum or a synthetic or semi-synthetic oleaginous liquid fraction, or a mixture thereof;
   (d) about 0.25 to about 2 wt-% of a $C_{16-18}$ aliphatic straight or branched chain fatty alcohol or fatty acid, or a mixture thereof;
   (e) about 1 to about 5 wt-% propylene glycol;
   (f) about 1 to about 3 wt-% glyceryl stearate;
   (g) about 0.01 to about 0.5 wt-% xanthan gum; and
   (h) the balance being water.

2. The composition of claim 1, wherein the antifungal agent is miconazole nitrate.

3. A method of treating onychomycosis comprising administering either concurrently or non-concurrently to a nail area of a patient in need thereof a composition according to claim 1.

4. A topical antifungal composition for treating onychomycosis consisting essentially of up to 5 wt.% of an antifungal agent in admixture with a tissue softening composition, wherein the tissue softening composition comprises:
   (a) about 40 wt-% urea;
   (b) about 5.5 to about 20 wt-% petrolatum or a synthetic or semi-synthetic hydrocarbon, or a semi-solid mixture thereof;
   (c) about 10 to about 20 wt-% of a liquid petrolatum or a synthetic or semi-synthetic oleaginous liquid fraction, or a mixture thereof;
   (d) about 0.25 to about 2 wt-% of a $C_{16-18}$ aliphatic straight or branched chain fatty alcohol or fatty acid, or a mixture thereof;
   (e) about 1 to about 5 wt-% propylene glycol;
   (f) about 1 to about 3 wt-% glyceryl stearate;
   (g) about 0.01 to about 0.5 wt-% xanthan gum;
   (h) about 0.05 to about 30 wt-% of a mixture of a carbomer and triethanolamine; and
   (i) the balance being water.

5. The composition of claim 4, wherein the antifungal agent is miconazole nitrate.

6. A method of treating onychomycosis comprising administering either concurrently or non-concurrently to a nail area of a patient in need thereof a composition according to claim 4.

7. A method of treating onychomycosis comprising using a kit which consists essentially of (a) a first dosage form of a tissue softening composition comprising an effective amount of urea and the balance being dermatologically acceptable excipients;
(b) a second unit dosage form of an antifungal composition comprising an antifungal agent and a pharmaceutically acceptable carrier;
(c) an occlusive dressing; and
(d) a protective gel; to a nail area of a patient in need thereof.

8. The kit of claim 7, wherein the tissue softening composition comprises about 40 wt-% urea.

9. The kit of claim 7, wherein the unit dosage forms are topical cream compositions.

10. The kit of claim 7, wherein the first and second unit dosage forms are mutually distinguishable by a visible feature.

11. The kit of claim 7, wherein the dressing is a toe shield dressing.

12. The kit of claim 7, wherein the protective gel is petroleum jelly.

* * * * *